United States Patent
Okamura et al.

(10) Patent No.: US 9,480,442 B2
(45) Date of Patent: Nov. 1, 2016

(54) ACCESSORY MOUNTING DEVICE AND ACCESSORY HAVING THE SAME FOR A RADIOGRAPHIC APPARATUS

(71) Applicants: Takayoshi Okamura, Kyoto (JP); Koji Yoshida, Kyoto (JP)

(72) Inventors: Takayoshi Okamura, Kyoto (JP); Koji Yoshida, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 246 days.

(21) Appl. No.: 14/157,120

(22) Filed: Jan. 16, 2014

(65) Prior Publication Data

US 2015/0196259 A1    Jul. 16, 2015

(51) Int. Cl.
*E05C 3/02*      (2006.01)
*A61B 6/04*      (2006.01)
*A61G 13/10*      (2006.01)

(52) U.S. Cl.
CPC ............ *A61B 6/0407* (2013.01); *A61G 13/10* (2013.01); *A61G 2203/78* (2013.01); *A61G 2210/50* (2013.01); *F16M 2200/02* (2013.01)

(58) Field of Classification Search
CPC ................ Y10T 292/1043; Y10T 292/1046; Y10T 292/1047
USPC ........... 292/97, 98, 100, 123, 124, 126, 196, 292/197, 200, 222, 223, 224, 226, 257
See application file for complete search history.

(56) References Cited

U.S. PATENT DOCUMENTS

| | | | | | |
|---|---|---|---|---|---|
| 1,553,712 | A * | 9/1925 | Myers | ............. | E05F 11/00 292/111 |
| 3,045,465 | A * | 7/1962 | Larson | ............. | E05C 3/162 292/223 |
| 4,159,137 | A * | 6/1979 | Richter | ............. | E05C 3/08 292/123 |
| 4,205,867 | A * | 6/1980 | Loikitz | ............. | E05B 65/0042 292/223 |
| 4,960,297 | A * | 10/1990 | Bouse | ............. | E05C 3/162 126/197 |
| 5,462,318 | A * | 10/1995 | Cooke | ............. | E05C 19/14 292/113 |
| 8,651,535 | B2 * | 2/2014 | Oppel | ............. | A47L 15/4259 292/100 |
| 2006/0119108 | A1 * | 6/2006 | Heid | ............. | E05B 15/0006 292/97 |
| 2013/0015670 | A1 * | 1/2013 | Perkins | ............. | E05B 81/28 292/97 |

* cited by examiner

*Primary Examiner* — Matthew Ing
(74) *Attorney, Agent, or Firm* — Andrew F. Young, Esq.; Lackenbach Siegel, LLP (57) ABSTRACT

An accessory mounting device and system for the same, particularly involving radiographic systems, includes a feature to securely recognize a fixing condition of an accessory. In mounting a platform to a table, a fixing member is oscillated or moved so that the platform moves to an engagement position. A pin installed at a tip of the fixing member engages a fixing element formed in the table. Then, a movement restriction member is oscillated so that it can move to a restriction position. An oscillating movement of the movement restriction member is restricted by moving a lock-pin. Alternatively, a fixing member in a movable non-lock-state allows a display region recognizable from a display position.

15 Claims, 4 Drawing Sheets

ACCESSORY MOUNTING DEVICE AND ACCESSORY HAVING THE SAME FOR A RADIOGRAPHIC APPARATUS

CROSS REFERENCE TO RELATED APPLICATIONS

This application relates to, but does not claim priority from, JP Ser. No. 2011-165437, filed Feb. 28, 2011 and published as JP Pub. No. 2013-27542 on Feb. 7, 2013; and JP Ser. No. 2011-165438 filed Jul. 28, 2011 and published as JP Pub. No. 2013-27543 on Feb. 7, 2013, the entire contents of each of which are incorporated herein fully by reference.

FIGURE SELECTED FOR PUBLICATION

FIG. 7A & 7B are selected for publication

BACKGROUND OF THE INVENTION

1. Field of the Invention

The present invention relates to an accessory mounting device to mount an accessory used for X-ray radiography to a table of a radiographic apparatus and an accessory having the accessory mounting device.

2. Description of the Related Art

With regard to a radiographic apparatus including an X-ray fluoroscopic radiography table, an accessory such as a platform on which a subject stands or a radiography trestle on which a subject sits down is used. The accessory used for the X-ray radiography is fixed to a concave element formed in the side of the table of the X-ray radiographic apparatus using a pin. (Patent Document 1).

Related Art includes Utility Model JP S59-156607, the content of which is incorporated fully by reference.

ASPECTS AND SUMMARY OF THE INVENTION

As provided herein, an accessory mounting device and system for the same, particularly involving radiographic systems includes a feature to securely recognize a fixing condition of an accessory. In mounting a platform to a table, a fixing member is oscillated so that the platform moves to an engagement position. A pin installed at a tip of the fixing member engages a fixing concave element formed in the table. Then, a movement restriction member is oscillated so that it can move to a restriction position. An oscillating movement of the movement restriction member is restricted by moving a lock-pin. Alternatively, a fixing member in a movable non-lock-state allows a display region recognizable from a display position.

In response, it is now recognized that there are several problems to be addressed with alternative and adaptive solutions proposed.

Problems to be Solved by the Invention

To provide an accessory mounting device that can securely recognize fixing condition of an accessory, and to provide the accessory including the same.

Proposed Solution(s)

When mounting a platform to a table, a fixing member is oscillated so that the platform moves to an engagement position. Thereby, a pin installed at the tip of the fixing member engages with a fixing concave element formed in the table. Then, a movement restriction member is oscillated so that it can move to a restriction position. Further, an oscillating movement of the movement restriction member is restricted by moving a lock-pin downward. Alternatively, at this time in a related embodiment, a display region is recognized from outside through a lock-state display window or hole. On the other hand, when a fixing member is in the movable non-lock-state, a different display region is recognized from outside through the lock-state display window. It is recognized that the display regions may include distinguishing indicia.

In one alternative aspect of the present invention, a table of a radiographic apparatus such as an X-ray transmissive radiography table should be changed in the direction from horizontal to standing or be turned around, by changing an angle thereof. Accordingly, when an accessory such as the platform or a radiography trestle is fixed insufficiently to the table, the fixing condition thereof should be securely assured because the patient during an examination may fall down from the platform or the radiography trestle. Accordingly, an operator traditionally assures the fixing condition by e.g. oscillating these accessories to right and left, but in fact it has been difficult to assure the fixing condition of the accessory by such operation. As a result, one aspect of the present invention provides an accessory mounting device that can securely recognize the fixing condition of the accessory, and to provide the accessory having the same.

According to another alternative aspect of the present invention, there is provided an accessory mounting device to mount an accessory used on an X-ray radiography to a table of a radiographic apparatus comprising, a pin engageable with a fixing concaved element formed in the table, a fixing member movable between an engagement position where the pin is engaged with the fixing concaved element and a distant position where the pin is distant from the fixing concave element, a movement restriction member is movable between a restriction position restricting said fixing member arranged at said engagement position to move from the engagement position to said distant position, and a save position allowing said fixing member to move between said engagement position and said distant position; and a lock mechanism to prevent the movement of the movement restriction member under the condition in which the movement restriction member is arranged at the restriction position.

According to another alternative aspect of the present invention, there is provided an accessory mounting device and system wherein the fixing member consists of a mechanism that allows to oscillate between the engagement position and the distant position and is biased toward the engagement position direction by the first spring; and the movement restriction member consists of a mechanism that allows to oscillate between the restriction position overlapped with the region where the fixing member is arranged when the fixing member moves to the distant position and a save position where is the distant region from the region where the fixing member is arranged when said fixing member moves to the distant position, and is biased toward the restriction position by a second spring.

According to another alternative aspect of the present invention, there is provided a lock mechanism consists of a mounting plate wherein a hole element is formed having a curve element having a curvature corresponding to the oscillation action of the movement restriction member and a liner element coupling on the curve element; and a lock-pin that is installed as movable for the movement restriction member and movable between the position inside the coupling element of the curve element and the linear element at the hole element under and engaging condition with the hole element.

According to another alternative aspect of the present invention, wherein the fixing member consists of a mechanism that allows to oscillate between said engagement position and said distant position and is biased toward the engagement position direction by the first spring; and the movement restriction member consists of a mechanism that allows to move in parallel between the restriction position overlapped with the region where the fixing member is arranged when the fixing member moves to the distant position and the save position where is the distant region from the region where said fixing member is arranged when said fixing member moves to the distant position, and is biased toward the restriction position by a second spring.

According to another alternative aspect of the present invention, there is provided a lock mechanism comprising: a mounting stand where a hole element having the first linear element facing the parallel movement direction of the movement restriction member, the second linear element facing the different direction from the direction of the first linear element coupling on the first linear element is formed; and a movement restriction member, and is movable between the position in the coupling element of the first linear element and the second linear element at the hole element under engagement condition with the hole element.

According to another alternative aspect of the present invention, wherein the accessory is a platform wherein a subject stands up or is a radiography trestle where a subject sits down.

According to another alternative aspect of the present invention, there is provided an accessory mounting device characterized in that a pair thereof is installed at a corresponding position to both right and left ends of the table.

According to another alternative aspect of the invention, the effect of the invention is that a fixing member is arranged at the engagement position, and a movement restriction member is arranged at the restriction position, wherein the locking status by the lock mechanism is assured since the lock mechanism prevents the movement of the movement restriction member, i.e. an movement of the fixing member so that the fixing status of the accessory can be surely recognized.

According to another alternative aspect of the present invention, there is provided an accessory mounting device arranged at positions corresponding to both right and left ends of the table to allow the accessory to be fixed surely to the table.

According to another alternative aspect of the present invention, there is provided an accessory mounting device, wherein the accessory mounting device is to mount an accessory used on an X-ray radiography to a table of an X-ray radiographic apparatus, comprising; a pin engageable with a fixing concaved element formed in the table; an engagement position where the pin engages with the fixing concave element, is movable between an engagement position where the pin engages with the concave element and a distant position where the pin is distant from the fixing concave, a movement restriction member movable between a restriction position restricting said fixing member arranged at said engagement position to move from said engagement position to said distant position and a save position allowing the fixing member to move between the engagement position and the distant position; and a movement restriction member in which a pair of display regions having different color or pattern is formed respectively, and a lock-state display window whereby only either one of the pair of the display regions can be visually recognized from outside along with movement between the restriction position and the save position of the movement restriction member.

According to another alternative aspect of the present invention, there is provided a fixing member, wherein the fixing member consists of a mechanism that allows to oscillate between the engagement position and the distant position and is biased in the engagement position one-direction by the first spring; and the movement restriction member consists of a mechanism that allows to oscillate between the restriction position overlapped with the region where the fixing member is arranged when the fixing member moves to the distant position and a save position where is the distant region from the region where the fixing member is arranged when said fixing member moves to the distant position, and is biased toward the restriction position by a second spring.

According to another alternative aspect of the present invention, there is provided a casing housing the fixing member and the movement restriction member, wherein the lock-state display window is a hole element formed in the region corresponding to the oscillation region of the pair of the display regions of the movement restriction member in the casing.

According to another alternative aspect of the present invention, there is provided an accessory, wherein the accessory is a platform where a subject stands up or a radiography trestle where a subject sits down.

According to another alternative aspect of the present invention, there is provided an accessory mounting device characterized in that a pair thereof is installed at a corresponding position of both the right and left ends of the table.

According to another alternative aspect of the present invention, there is provide in improvement wherein either one of the display regions is displayed in the state in which the fixing member is positioned in the engagement position and the movement restriction member is positioned in the restriction position, whereby accordingly, the lock-state can be confirmed by visually recognizing any display regions in the lock-state display window so that the accessory is surely fixed to the table.

According to another alternative aspect of the present invention, the accessory mounting devices are arranged at the positions corresponding to both right and left ends of the table allow the accessory to be fixed surely to the table.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 9 illustrates an explanatory drawing to explain the relationship between a hole element 49 formed in the mounting stand 45 and a lock-pin 42 installed in a movement restriction member 43a.

FIG. 10 illustrates a front view of a movement restriction member 43a.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple', 'connect', 'join', 'communicate' and similar terms do not necessarily denote direct and immediate connections, but also include connections through intermediate elements or devices. It will be understood, that suitable operable connectors and linkages and devices exist herein as needed for the proposed invention and the methods of use and manipulation will be readily understood by those of skill in the art as being included herein following study of the present disclosure. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the preferred embodiment descriptions herein are not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent or that steps may not be replaced, modified, or that intermediate steps may not be conducted within the scope of the invention.

The present invention is now illustrated below in various non-limiting embodiments. According to the present invention, radiography or X-ray descriptions correspond to a radiation of the present invention, but other forms of radiation may be used without departing from the invention.

Embodiments of the present invention are now illustrated referring to figures.

Selected Embodiments of the Invention

It will be understood by those of skill in the art that the phrases radiography will be noted as descriptive of a process, method, or apparatus or system for taking images of opaque objects, typically with X-ray radiation (although not limited thereto). These operations shall be understood as descriptive within the field of art and understood by those skilled therein as being within the scope and spirit of the present invention.

Figure 1:
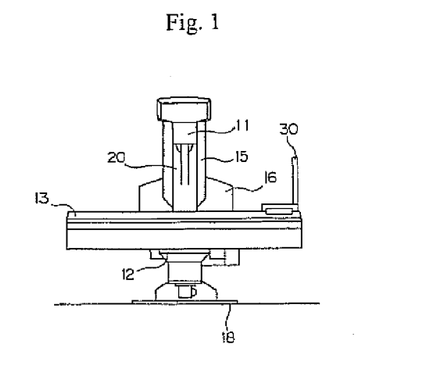
FIG. 1 illustrates a schematic view of a radiographic examination apparatus according to one aspect of the present invention, which is a front view when a table 13 is arranged in a lie position.
Figure 2:
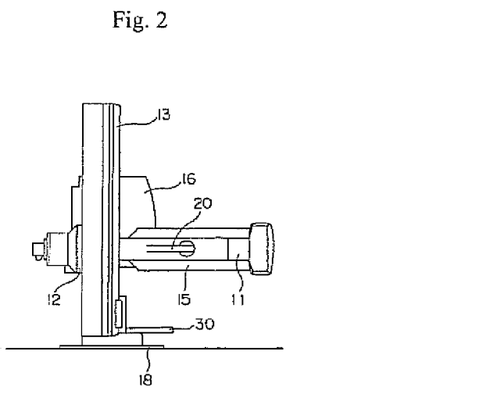
FIG. 2 illustrates a schematic view of a radiographic examination apparatus according to one aspect of the present invention, which is a front view when a table 13 is arranged in a stand position.
Figure 3:
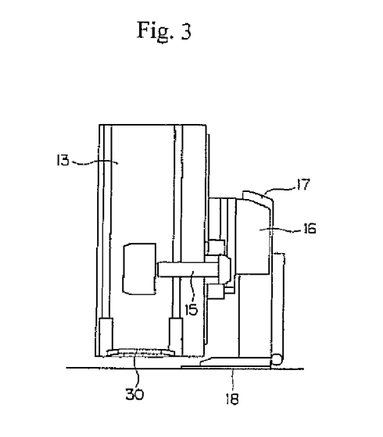
FIG. 3 illustrates a schematic view of a radiographic examination apparatus according to one aspect of the present invention, which is a side view when a table 13 is arranged in a stand position.

The inventors further illustrate Embodiments of the present invention following figures. FIG. 1 to FIG. 3 are schematic views of a radiographic examination apparatus according to the present invention. FIG. 1 is a front view of a radiographic examination apparatus when a table 13 is arranged in a lie position. FIG. 2 is a front view of a radiographic examination apparatus when a table 13 is arranged in a stand position. FIG. 3 is a side view of a radiographic examination apparatus when a table 13 is arranged in a stand position.

The radiographic examination apparatus is known as an X-ray fluoroscopic table comprising a table 13, a slide arm 15 coupled on the table 13, an X-ray tube 11 arranged at a tip of the slide arm 15, and a flat panel detector 12 as an X-ray detector installed at the opposite side of the X-ray tube 11 relative to the table 13. A compression cylinder mechanism 20 that compresses a diagnostic part of the subject in accordance with necessity is installed at the slide arm 15. Further, a platform 30 as an accessory of the present invention is fixed to the table 13.

The table 13, the slide arm 15 and the X-ray tube 11 are turnable or rotatable between the lie position where the surface of the table 13 faces the horizontal direction as shown in FIG. 1 and a stand position where the surface of the table 13 faces the vertical direction as shown in FIGS. 2 and 3 by a rotation mechanism 16 having a motor inside, not shown in FIG. Further, the rotation mechanism 16 per se moves up and down along a main support 17 vertically installed on a base plate 18.

When the table 13 is in the lie position, fluoroscopy and radiography for the lying subject can be conducted. At this time, the subject is loaded on the table 13. When the table 13 is in the stand position, fluoroscopy and radiography for the standing subject can be conducted. Further, when the radiography is conducted while changing the angle of the table 13, the subject stands up on the platform 30 fixed to the table 13. Then, the angle of the table 13 is changed while the subject is being on the platform. Referring to FIG. 1, the platform 30 is mounted to or demounted from the table 13 when the table 13 is in the lie position. Meantime, when a fluoroscopy or radiography is conducted on the lying subject, the platform 30 is demounted from the table 13.

Figure 4A:
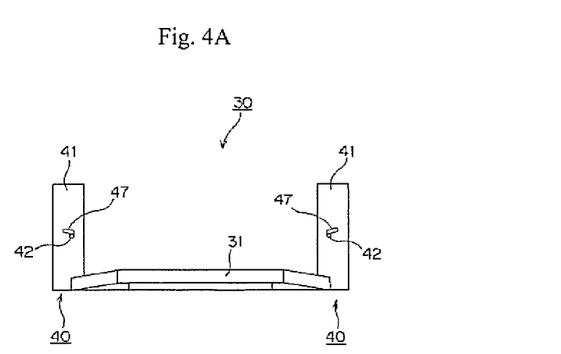
FIG. 4A illustrates a front view of a platform 30.
Figure 4B:
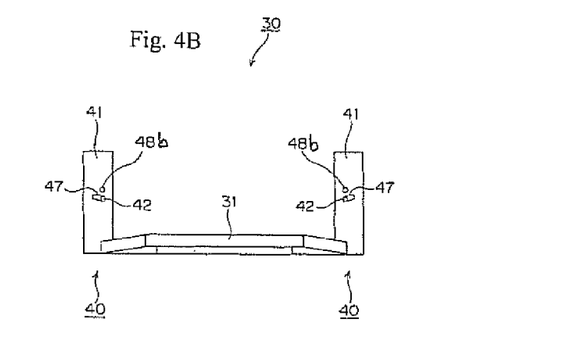
FIG. 4B illustrates a front view of a platform 30 with an additional feature.
Figure 5:
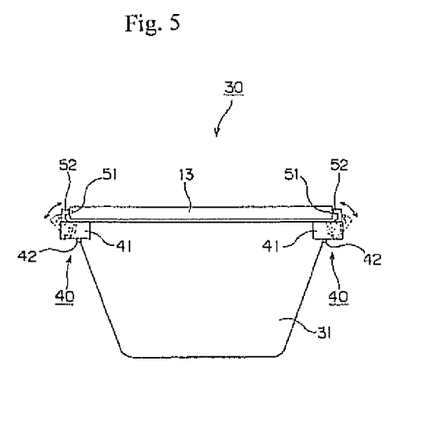
FIG. 5 illustrates a plan view of a platform 30 with a table 13.
Figure 6:
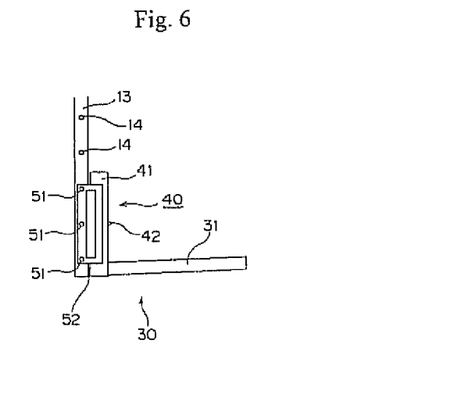
FIG. 6 illustrates a side view of a platform 30 with a table 13.

Next, the inventors illustrate a structure of a platform 30 of the present invention as an accessory. FIGS. 4A and 4B illustrate respective front views of a platform 30. FIG. 5 illustrates a plan view of a platform 30 with a table 13. Further, FIG. 6 illustrates a side view of a platform 30 with a table 13. Meantime, a pin 51 located in the other side of a fixing member 52 is shown as a solid line.

The platform 30 adaptively comprises a footboard 31 and a pair of mounting elements 40 installed in both right and left sides of the footboard 31. Each mounting element 40 comprises a casing 41. In one type of mounting element 40, a fixing member 52 having a pin 51 at the tip thereof, and an operational lock-pin 42 arranged inside of a hole element 47 drilled in the casing 41. In another type of mounting element 40, the casing 41 adaptively includes a lock-state display window 48*b* (as illustrated) which is later drilled and installed for visual review as will be discussed. These pairs of mounting elements 40 consist of the structure in which the entire platform 30 is mounted to the table 13 by engaging with the pin 51 at the tip of the fixing member 52 installed for plural fixing concaves 14 (referring to FIG. 6) formed in the table 13. Meantime, the mounting element 40 constitutes an accessory of the present invention.

Figure 9:
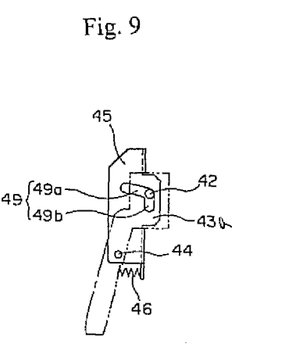
Figure 10:
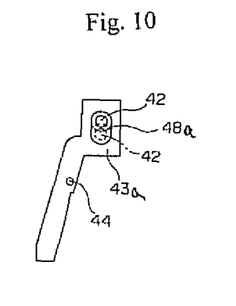

Next, the inventors illustrate the structure of on version of a mounting element 40. FIGS. 7A, 7B, 8A, and 8B illustrate a schematic view of one version of the mounting element 40. In these FIG. (A) illustrate a brief plan view and (B) illustrates a brief front view. FIG. 9 illustrates an explanatory drawing to explain the relationship between a hole element 49 formed in the mounting plate 45 and a lock-pin 42 installed in a movement restriction member 43*a*, and FIG. 10 is a front view of the movement restriction member 43*a*. Meantime, the mounting plate 45 is drawn as it is arranged at the backside of the movement restriction member 43*a* in FIG. 7B and FIG. 8B for the sake of convenience of explanation, and only the hole element 49 thereof is drawn in the front side of the movement restriction member 43*a*

As described above, the version of the mounting element 40 show here comprises a fixing member 52 having a pin 51 at the tip thereof. The fixing member 52 can be oscillated around the axis 53 as the center thereof and is biased in the clockwise direction at FIG. 7A and FIG. 8A by the action of a spring 54. As described later, the fixing member 52 can be oscillated between a distant position shown in FIG. 7A/B and an engagement position in FIG. 8A/B. Further, the mounting element 40 comprises the movement restriction member 43*a* that can be oscillated around the axis 44 as the center thereof. The fixing member 43*a* is biased in the clockwise direction at FIG. 7A and FIG. 8B by the action of a spring 46. As described later, the fixing member 43*a* can be oscillated between a safe position shown in FIGS. 7A/B and a restriction position in FIGS. 8A/B.

Further, the mounting element 40 comprises a mounting stand 45 coupled on and fixed to a casing 41. An axis 44 as the oscillation center of the movement restriction member 43*a* is installed on the mounting stand 45. Further, a hole element 49 is formed in the mounting stand 45. Referring to FIG. 9, the hole element 49 comprises a curve element 49*a* having a curvature corresponding to oscillation movement of the movement restriction member 43*a* and a linear element 49*b* coupling on the curve element. Referring to FIG. 10, the movement restriction member 43*a* comprises a lock-pin 42. The lock-pin 42 has a double-deck structure consisting of a small diameter element and a large diameter element. Further, the tip element that is the small element of the lock-pin 42 engaging with the hole element 49 as illustrated in FIGS. 7A through FIG. 9. Further, the lock-pin 42 is movable inside the slide hole 48*a* formed in the movement restriction member 43*a* in the up-and-down direction.

Figure 7A:
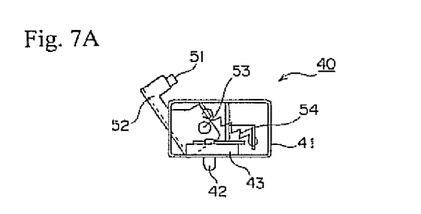
FIGS. 7A and 7B illustrates a schematic view of a mounting element 40.
Figure 7B:
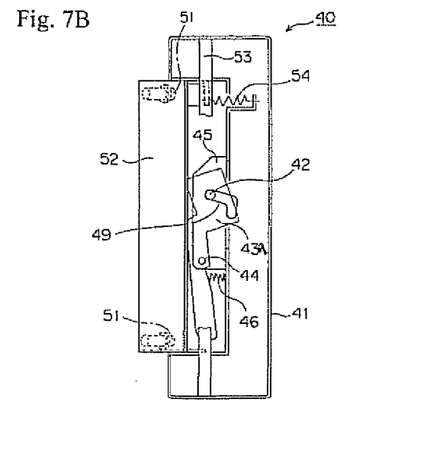

Referring to FIG. 7A/B, in this version of the mounting element 40 consisting of the above arrangement, the movement restriction member 43*a* is moved to the safe position by oscillating in the counter clockwise direction as shown in FIG. 7B as the axis 44 is center while against the bias force due to the spring 46 by operating the lock-pin 42, and the fixing member 52 is moved to the distant position by oscillating in the counter clockwise direction as shown in FIG. 7A as the axis 53 is center while against the bias force due to the spring 54, and whereby the platform 30 can be mounted to the table 13 or demounted from the table 13.

Figure 8A:
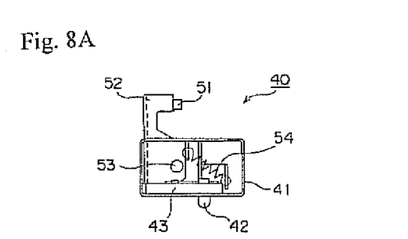
FIGS. 8A and 8B illustrates a schematic view of a mounting element 40 of FIGS. 7A, 7B now in a different position.

Referring to FIGS. 8A/B, the platform 30 is mounted to the table 13; the fixing member 52 is moved to the engagement position by oscillating in the counter clockwise direction as shown in FIG. 7A as the axis 53 is a center. Accordingly, referring to FIGS. 5 and 6, a pin 51 installed at the tip of the fixing member 52 engages with the fixing concave element 14 formed in the table 13 so that the platform 30 can be fixed to the table 13.

At this state, this version of the movement restriction member 43*a* is moved to the restriction position by oscillating in the clockwise direction as shown in FIG. 7B as the axis 44 is center by operating the lock-pin 42. Accordingly, referring to FIGS. 8A/B, the movement restriction member 43*a* is arranged in the region where the fixing member 52 must be arranged when it moves to the distant position. Accordingly, the fixing member 52 arranged in the engagement position can be restricted to move to the distant position shown in FIGS. 7A/B from the engagement position by the action of the movement restriction member 43*a* arranged at the restriction position.

Figure 8B:
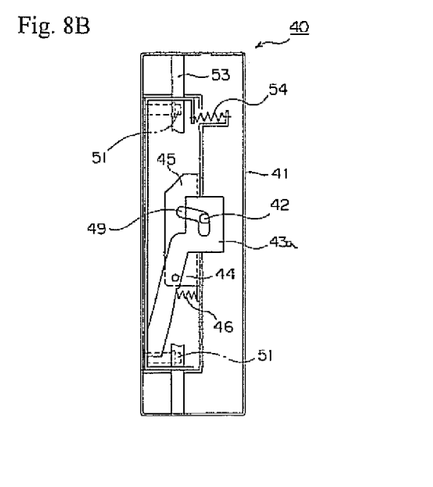

Further, at this state, the lock-pin 42 is moved downward, as it shown as virtual line (see dashed lining) in FIG. 10, from the state shown in FIGS. 8A/B through FIG. 10. Specifically, as shown in FIGS. 8A/B through FIG. 10, the lock-pin 42 engaging with the hold element 49 is moved from the intersection point, where a curve element 49*a* having a curvature corresponding to an oscillation action of the movement restriction member 43*a* and a line element 49*b* coupling on the curve element 49*a* intersect, to the lower end of the line element 49*b*. Accordingly, the oscillating action of the movement restriction member 43*a* is restricted and the movement restriction member 43*a* is fixed in the restriction position shown in FIGS. 8A through FIG. 10. Therefore, it is possible that the fixing member 52 arranged in the engagement position is restricted to move the distant position.

On the other hand, when this platform 30 is demounted from the table 13, the lock-pin 42 is moved upward. Accordingly, referring to FIGS. 8A through FIG. 10, the lock-pin 42 moves from the low end of the linear element 49*b* to the intersection of the curve element 49*a* and the linear element 49*b*. Accordingly, it can be possible that the movement restriction member 43*a* is moved to the safe position by oscillating in the counterclockwise direction as shown in FIG. 7B as the axis 44 is center. Then, it is in the state wherein the fixing member 52 is moved to the distant position by oscillating in the counterclockwise direction as shown in FIG. 7A as the axis 53 is center so that the engagement relationship between the pin 51 and the fixing concave element 14 formed in the table 13 is released and accordingly the platform 30 can be demounted from the table 13.

Meantime, in the state shown in adaptive FIGS. 7A/B, it is not possible for the lock-pin 42 to be moved downward because the lock-pin 42 is engaged with the curve element 49*a* of the hole element 49. Specifically, from the structure standpoint, the lock-pin 42 cannot move to the position for locking; unless the fixing member 52 moves to the engagement position and the pin 51 and the concave element 14 formed in the table 13 are engaged, and further, it is the state in which this adaptive movement restriction member 43*a* moves to the restriction position and the oscillation of the fixing member 52 is being restricted. Therefore, when the lock-pin 42 has been moved downward, the platform 30 is assuredly fixed to the table 13 so that it can surely recognize the fixing state of the platform 30.

Figure 12A:
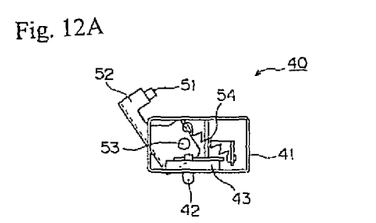
FIGS. 12A and 12B illustrate a schematic view of a mounting element 40 according to another embodiment.
Figure 12B:
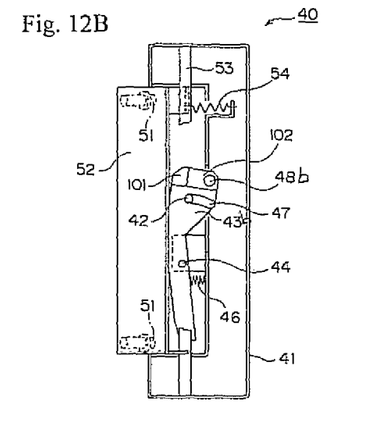
Figure 13A:
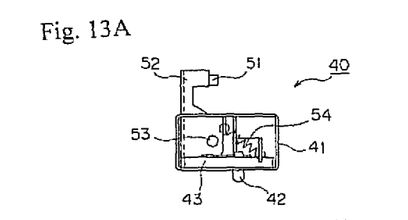
FIGS. 13A and 13B illustrate a schematic view of a mounting element 40 according to another embodiment as in FIGS. 12A and 12B in a different position.
Figure 13B:
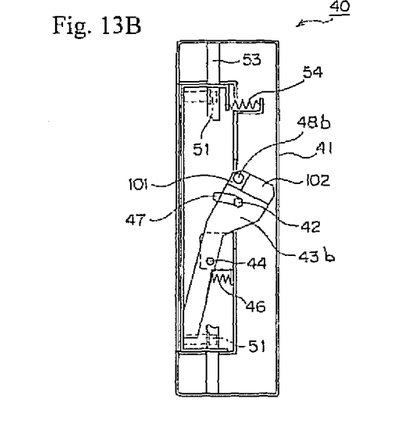

Next, the inventors illustrate a further adaptive and alternative structure for mounting element 40. FIGS. 12A, 12B and 13A and 13B illustrate an alternative schematic view of the mounting element 40. In these FIGS. 12A, 13A illustrate an overview of a plan view and FIGS. 12B, 13B illustrate an overview of a front view. Further, a hole element 47 formed in a casing 41 and a lock-state display window 48b are shown in these Figures.

As described above, this version of mounting element 40 (similar to that discussed above) comprises fixing member 52 having pin 51 at the tip thereof. The fixing member 52 can be oscillated around the axis 53 as the center thereof and is biased in the clockwise direction at FIG. 12A and FIG. 13A by the action of a spring 54. As described later, the fixing member 52 can be oscillated between a distant position shown in FIGS. 12A/B and an engagement position in FIGS. 13A/B. Further, this version of the mounting element 40 comprises a movement restriction member 43b that can be oscillated around the axis 44 as the center thereof. The fixing member 43b is biased in the clockwise direction at FIG. 12B and FIG. 13B by the action of spring 46. As described later, the fixing member 43b can be oscillated between a safe position shown in FIG. 12A/B and a restriction position in FIG. 13A/B.

Figure 14:
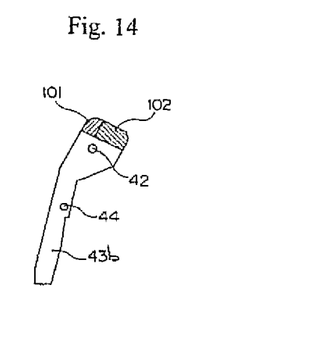
FIG. 14 illustrates a front view of a movement restriction member 43b according to an alternative embodiment.

FIG. 14 illustrates a front view of a movement restriction member 43b.

In this adaptive embodiment, the above operation pin 42 is installed in stand to the movement restriction member 43b. Further, one pair of display regions 101, 102 each having different indicia (e.g., color and/or patterns from each other) is formed at the end element of the movement restriction member 43b. Display regions 101, 102 are positioned at the position distant from the axis 44 in the same distance each other. Specifically, these pairs of the display regions 101, 102 are arranged concentrically as the axis 44 is center. Accordingly, during use the movement restriction member 43b oscillates about axis 44 as a center so that the display regions 101, 102 can change the position thereof each other.

Further, in this adaptive embodiment, the distance between the lock-state display window 48b and the axis 44 is the same as the distance between the display region 101, 102 and the axis 44. Specifically, the lock-state display window 48b consists of a hole element formed in the region corresponding to the oscillation region of the pair of the display regions 101, 102 of the movement restriction member 43b in the casing 41.

Referring to FIGS. 12A/B, in this version of the mounting element 40 consisting of the above arrangement, the movement restriction member 43b is moved to the safe position by oscillating in the counter clockwise direction as shown in FIG. 12B as the axis 44 is center while against the bias force due to the spring 46 by operating the lock-pin 42, and the fixing member 52 is moved to the distant position by oscillating in the counter clockwise direction as shown in FIG. 12A as the axis 53 is center while against the bias force due to the spring 54, and whereby the platform 30 can be mounted to the table 13 or demounted from the table 13.

In this state referring FIG. 12B, the display region 102 is arranged in the position facing against the lock-state display window 48b. Accordingly, only a display region 102 is recognized from outside through a lock-state display window 48.

Referring to FIGS. 13A/B, the platform 30 is mounted to the table 13, the fixing member 52 is moved to the engagement position by oscillating in the counter clockwise direction as shown in FIG. 12A as the axis 53 is center Accordingly, referring to FIG. 5 and FIG. 6, pin 51 installed at the tip of the fixing member 52 engages with fixing concave element 14 formed in the table 13 so that the platform 30 can be fixed to the table 13.

And the movement restriction member 43b is moved to the restriction position by oscillating in the clockwise direction as shown in FIG. 12B as the axis 44 is center by operating the lock-pin 42. Accordingly, referring to FIGS. 13A/B, the movement restriction member 43b is arranged in the region where the fixing member 52 must be arranged when it moves to the distant position. Accordingly, the fixing member 52 arranged in the engagement position can be restricted to move to the distant position shown in FIGS. 12A/B from the engagement position by the action of the movement restriction member 43b arranged at the restriction position.

In this state referring FIG. 13B, the display region 101 is arranged in the position facing against the lock-state display window 48b. At this time, a display region 101 is recognized from outside through a lock state display window 48b.

Accordingly, as to this version of the mounting element 40, in the lock-state wherein the fixing member 52 is restricted, the display region 101 is visually recognized from outside through the lock-state display window 48b and in the non-lock-state wherein the fixing member 52 is movable, the display region 102 is visually recognized from outside through the lock-state display window 48b. Accordingly, any display region can be visually recognized through the lock-state display window 48b so that the lock-state of the mounting element 40 can be easily recognized. It will be understood, that multiple display regions can be used.

Further, as noted in FIG. 14, the display region 101 and the display region 102 are preferably colored or having easily-viewed indicia e.g., green and red, which are different each other and can be easily distinguished. Further, any different patterns (e.g., lines, symbols etc.) with or without spaces can be easily recognized therefrom by even a person having a defect in color perception. Even further preferably, both color and pattern can be different.

Figure 11:
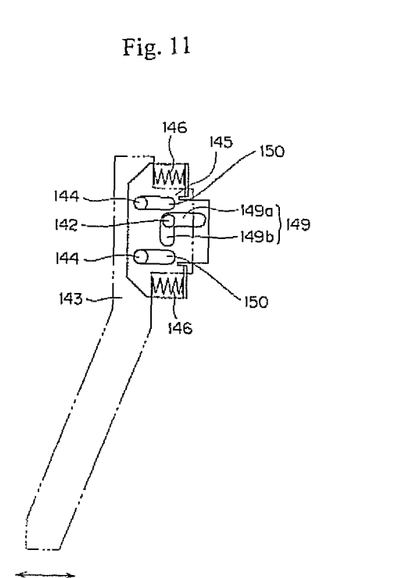
FIG. 11 illustrates an explanatory drawing to explain the relationship between a hole element 149 formed in the mounting stand 145 and a lock-pin 142 arranged in a movement restriction member 143 according to another embodiment.

Referring now to another adaptive version of the proposed inventive details, the inventors of the present invention illustrates another embodiment of a mounting element 40. Referring now additionally to FIG. 11 which illustrates an explanatory drawing to explain the relationship between a hole element 149 formed in the mounting stand 145 and a lock-pin 142 installed in a movement restriction member 143 according to another embodiment of the present invention.

According to the above embodiment, while the movement restriction member 43 (either 43a or 43b) structure-wise oscillates (rotate), in this embodiment, the movement restriction member 143 structure-wise moves in parallel (a non-rotation-type motion); and further while in the above embodiment (see FIG. 9 et seq.), while the lock-pin 42 engages with the hole element 49 consisting of the curve element 49a and the linear element 49b, in this embodiment (FIG. 11), the lock-pin 142 engages with the hole element 149 consisting of the first linear element 149a and the second linear element 149b; and therefore both embodiment are different each other. Further detail of this embodiment is skipped because the other elements of this embodiment are the same as the above embodiment.

Movement restriction member 143 is biased in the left direction in FIG. 11 because of an action of a pair of springs 146. Further, according to the embodiment of the present invention, a pair of guide holes 150 with which a pair of pins 144 installed in standing in the movement restriction member 143 engages is formed in the mounting plate 145 according to this embodiment. Further, according to this embodiment, the hole element 149 engaging with the lock-pin 142 as well as in the above embodiment is formed on a mounting stand 145. The first linear element 149a facing the parallel movement direction of the movement restriction member 143 and the second linear element 149b coupled on the first linear element 149a and facing the vertical direction to the first linear element 149 are formed in the hole element 149.

According to this embodiment, the movement restriction member 143 is moved in the right direction in parallel, as wells as the above embodiment as shown in FIG. 11 against the bias force due to the spring 146 by operating the lock-pin 142, and (see in contrast at FIG. 9) the fixing member 52 is moved to the distant position by oscillating in the counterclockwise direction as the axis 53 is center while against the bias force due to the spring 54, and whereby the platform 30 can be mounted to the table 13 or demounted from the table 13. The end result being completed similarly.

When the platfomi 30 is mounted to the table 13, as wells as the above embodiment, the fixing member 52 (FIG. 9) is moved to the engagement position by oscillating in the clockwise direction as the axis 53 is center. Accordingly, referring to FIG. 5 and FIG. 6, a pin 51 installed at the tip of the fixing member 52 engages with the fixing concave element 14 formed in the table 13 so that the platform 30 can be fixed to the table 13.

At this state (FIG. 11), the movement restriction member 143 is moved to the restriction position by oscillating in the left direction as shown in FIG. 11 by operating the lock-pin 142. Accordingly, the movement restriction member 143 is arranged in the region where the fixing member 52 is arranged when it moves to the distant position. Accordingly, the fixing member 52 arranged in the engagement position can be restricted to move to the distant position from the engagement position by the action of the movement restriction member 143 adaptively arranged at the restriction position.

Further, at this state, the lock-pin 142 is moved downward from the state shown in FIG. 11. Specifically, the lock-pin 142 engaged with the hole element 149 is moved from the intersection of the first linear element 149a facing parallel movement direction of the movement restriction member 143 and the second linear element 149b facing the orthogonal direction to the first linear element 149a to the end of the second linear element 149b. Accordingly, the parallel movement action of the movement restriction member 143 is restricted and the movement restriction member 143 is fixed in the restriction position. Therefore, it is possible that the fixing member 52 arranged in the engagement position is restricted to move the distant position.

On the other hand, when the platform 30 is demounted from the table 13, the lock-pin 142 is moved upward. Accordingly, the lock-pin 42 moves from the low end of the second linear element 49b to the intersection of the first linear element 149a and the second linear element 149b. Accordingly, the movement restriction member 143 can be moved to the save position by being moved in parallel in the right direction. Then, the fixing member 52 is moved to the distant position by oscillating in the counterclockwise direction as the axis 53 is center so that the engagement relationship between the pin 51 and the fixing concave element 14 formed in the table 13 is released and accordingly the platform 30 can be demounted from the table 13.

Meantime, in the state wherein the lock-pin 142 is engaged with the first linear element 149, the lock-pin 142 cannot be moved downward even if it is tried to be moved downward. Specifically, from the structure standpoint, the lock-pin 142 cannot move to the position for locking; unless the fixing member 52 moves to the engagement position and the pin 51 and the concave element 14 formed in the table 13 are engaged, and further, it is the state in which the movement restriction member 143 moves to the restriction position and the oscillation of the fixing member 52 is being restricted. Therefore, when the lock-pin 142 has been moved downward, the platform 30 is assuredly fixed to the table 13 so that it can surely recognize the fixing state of the platform 30.

Meantime, according to each of the above alternative and adaptive embodiments, the invention can be applied for the platform where the subject stands as an X-ray radiography accessory, but also it can be applied for a radiography trestle where the subject sits down. Further, it can be applied to other accessories freely mounted to and demounted from a table 13.

REFERENCE NUMERALS

11 X-ray tube
12 Flat panel detector
13 Table
14 Fixing concave element
15 Slide arm
16 Rotation mechanism
17 Main supporting stand or column
18 Base plate
30 Platform
31 Footboard
40 Mounting element
41 Casing
42 Lock-pin or operation pin
43a Movement restriction member (see FIGS. 7A-10)
43b Movement restriction member (see FIGS. 12A-14)
44 Axis
45 Mounting plate
46 Spring
48a Slide hole (see FIG. 10)
48b Lock-state display window (see FIG. 4B, 12B, 13B)
49 Hole element
49a Curve element
47b Linear element
51 Pin
52 Fixing member
53 Axis
54 Spring
101 display region
102 display region
142 Lock-pin
143 Movement restriction member
144 Pin
145 Mounting plate
146 Spring
149 Hole element
149a First curve element
149b Second linear element It will be understood by those of skill in the art that the use of the phrases constitute, constitution, comprising, exemplary, embodiment, illustration, step, or system are provided as assistive aids to the reader and are not used to imply a required limiting arrangement or structure or assembly of features or aspects or functions or method steps to the invention. The aspects of the invention as discussed herein are to be considered broadly and without limitation. For example, the operative method steps may be modified for use during operation of the apparatus and systems proposed, such that multiple methods of operating the same may be readily accommodated without departing from the scope and spirit of the proposed invention. It will be further understood by those of skill in the art that the use of the phrase means may be interchangeably used with the phrase element, system, or feature, to be operably understood by those of suitable skill. Thus, that the feature, aspect, means, or element will be as described and function as enabled or described within the skill of one of the art.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure covers modifications and variation of this invention provided they come within the scope of the appended claims and their equivalents.

What is claimed is:

1. An accessory mounting device, wherein the accessory mounting device is operative to mount an accessory used in radiography to a spacing support of a radiographic apparatus, comprising:
   a fixing member having a pin engageable with a fixing concave element formed in said spacing support;
      said fixing member operative to move between an engagement position where said pin engages with said concave element and a distant position where said pin is distant from said fixing concave element;
   a movement restriction member;
      said movement restriction member operative to move between a restriction position wherein said movement restriction member operably restricts said fixing member arranged at said engagement position from moving from said engagement position to said distant position and a safe position operably allowing said fixing member to move between said engagement position and said distant position;
   a lock mechanism selectively operative to prevent an unintended movement of said movement restriction member from said restriction position to said safe position; and
   a bias member that provides a bias force to said movement restriction member in a direction toward said restriction position.

2. The accessory mounting device, according to claim 1, wherein:
   said fixing member further comprises:
      a first mechanism operative to allow an oscillation of said fixing member between said engagement position and said distant position;
      said first mechanism being biased toward said engagement position direction by a first spring;
   said movement restriction member further comprises:
      a second mechanism operative to allow said movement restriction member to move in parallel between said restriction position being overlapped with a first region wherein said fixing member is arranged when the fixing member moves to the distant position and said safe position which is distal from said first region wherein the fixing member is arranged when said fixing member moves to the distant position; and
      said second mechanism is biased toward said restriction position by a second spring.

3. The accessory mounting device, according to claim 2, wherein:
   said lock mechanism is operatively movable as a curve element having a curvature corresponding to an oscillation action of said movement restriction member and a coupling element;
   said accessory mounting device, further comprising:
      a mounting plate having a hole element defining a linear portion formed for operative coupling with said curve element and said movement restriction member during a use; and
      a lock-pin movable between a first position in said coupling element of said curve element and said linear portion of said hole element and a second position of said linear portion under an engagement condition with said hole element.

4. The accessory mounting device according to claim 2, wherein:
   said lock mechanism is movable as a mounting plate wherein a hole element includes a first linear portion facing a parallel movement direction of said movement restriction member and a second linear portion facing a different direction from said first linear portion and coupled with said first linear portion; and
   a lock-pin movable between a first position in said first linear portion of said coupling element and a second position in said second linear portion of said coupling element under engagement condition with said hole element.

5. The accessory mounting device, according to claim 2, further comprising:
   a casing housing said fixing member and said movement restriction member; and
   a lock state display window operatively formed as hole element formed in a region corresponding to an oscillation region of a pair of display regions defined on said movement restriction member in said casing.

6. The accessory mounting device, according to claim 1, wherein:
   said accessory mounting device is one of a first support operably arranged wherein an external subject stands up and a second support operably arranged wherein an external subject sits down.

7. The accessory mounting device, according to claim 1, further comprising:
   a pair of accessories installed at respective corresponding positions along both a respective first end and a second end of said spacing support.

8. An accessory mounting device, wherein the accessory mounting device is operative to mount an accessory used in radiography to a spacing support of a radiographic apparatus, comprising:
   a fixing member having a pin engageable with a fixing concave element formed in said spacing support;
      said fixing member operative to move between an engagement position where said pin engages with said concave element and a distant position where said pin is distant from said fixing concave element;
   a movement restriction member;

said movement restriction member operative to move between a restriction position wherein said movement restriction member operably restricts said fixing member arranged at said engagement position from moving from said engagement position to said distant position and a safe position operably allowing said fixing member to move between said engagement position and said distant position;

a lock mechanism selectively operative to prevent an unintended movement of said movement restriction member from said restriction position to said safe position;

said fixing member further comprises:
 a first mechanism operative to allow an oscillation of said fixing member between said engagement position and said distant position;
 said first mechanism being biased toward said engagement position direction by a first spring;

said movement restriction member further comprises:
 a second mechanism operative to allow said movement restriction member to move in parallel between said restriction position being overlapped with a first region wherein said fixing member is arranged when the fixing member moves to the distant position and said safe position which is distal from said first region wherein the fixing member is arranged when said fixing member moves to the distant position;
 said second mechanism is biased toward said restriction position by a second spring;

said lock mechanism is operatively movable as a curve element having a curvature corresponding to an oscillation action of said movement restriction member and a coupling element;

said accessory mounting device, further comprising:
 a mounting plate having a hole element defining a linear portion formed for operative coupling with said curve element and said movement restriction member during a use; and
 a lock-pin movable between a first position in said coupling element of said curve element and said linear portion of said hole element and a second position of said linear portion under an engagement condition with said hole element.

9. The accessory mounting device, according to claim 8, further comprising:
 a casing housing said fixing member and said movement restriction member; and
 a lock state display window operatively formed as hole element formed in a region corresponding to an oscillation region of a pair of display regions defined on said movement restriction member in said casing.

10. The accessory mounting device, according to claim 8, wherein:
 said accessory mounting device is one of a first support operably arranged wherein an external subject stands up and a second support operably arranged wherein an external subject sits down.

11. The accessory mounting device, according to claim 8, further comprising:
 a pair of accessories installed at respective corresponding positions along a respective first end and a second end of said spacing support.

12. An accessory mounting device, wherein the accessory mounting device is operative to mount an accessory used in radiography to a spacing support of a radiographic apparatus, comprising:

a fixing member having a pin engageable with a fixing concave element formed in said spacing support;
 said fixing member operative to move between an engagement position where said pin engages with said concave element and a distant position where said pin is distant from said fixing concave element;

a movement restriction member;
 said movement restriction member operative to move between a restriction position wherein said movement restriction member operably restricts said fixing member arranged at said engagement position from moving from said engagement position to said distant position and a safe position operably allowing said fixing member to move between said engagement position and said distant position;

a lock mechanism selectively operative to prevent an unintended movement of said movement restriction member from said restriction position to said safe position;

said fixing member further comprises:
 a first mechanism operative to allow an oscillation of said fixing member between said engagement position and said distant position;
 said first mechanism being biased toward said engagement position direction by a first spring;

said movement restriction member further comprises:
 a second mechanism operative to allow said movement restriction member to move in parallel between said restriction position being overlapped with a first region wherein said fixing member is arranged when the fixing member moves to the distant position and said safe position which is distal from said first region wherein the fixing member is arranged when said fixing member moves to the distant position;
 said second mechanism is biased toward said restriction position by a second spring;

said lock mechanism is movable as a mounting plate wherein a hole element includes a first linear portion facing a parallel movement direction of said movement restriction member and a second linear portion facing a different direction from said first linear portion and coupled with said first linear portion;

and a lock-pin movable between a first position in said first linear portion of said coupling element and a second position in said second linear portion of said coupling element under engagement condition with said hole element.

13. The accessory mounting device, according to claim 12, further comprising:
 a casing housing said fixing member and said movement restriction member; and
 a lock state display window operatively formed as hole element formed in a region corresponding to an oscillation region of a pair of display regions defined on said movement restriction member in said casing.

14. The accessory mounting device, according to claim 12, wherein:
 said accessory mounting device is one of a first support operably arranged wherein an external subject stands up and a second support operably arranged wherein an external subject sits down.

15. The accessory mounting device, according to claim 12, further comprising:

a pair of accessories installed at respective corresponding positions along a respective first end and a second end of said spacing support.

\* \* \* \* \*